(12) United States Patent
Viola et al.

(10) Patent No.: US 10,543,004 B2
(45) Date of Patent: Jan. 28, 2020

(54) BONE CENTERING DRILL GUIDE

(71) Applicant: OsteoMed LLC, Addison, TX (US)

(72) Inventors: Randall W. Viola, Vail, CO (US);
Nicholas Monks, Frisco, TX (US);
Joseph Pepin, Sachse, TX (US);
Eduardo Franco, The Colony, TX (US)

(73) Assignee: OsteoMed LLC, Addison, TX (US)

( * ) Notice: Subject to any disclaimer, the term of this patent is extended or adjusted under 35 U.S.C. 154(b) by 425 days.

(21) Appl. No.: 15/389,399

(22) Filed: Dec. 22, 2016

(65) Prior Publication Data

US 2017/0181757 A1 Jun. 29, 2017

Related U.S. Application Data

(60) Provisional application No. 62/387,220, filed on Dec. 23, 2015.

(51) Int. Cl.
*A61B 17/17* (2006.01)
(52) U.S. Cl.
CPC .................................. *A61B 17/17* (2013.01)
(58) Field of Classification Search
CPC ..... A61B 17/17; A61B 17/28; A61B 17/2812; A61B 17/2816; A61B 17/2833; A61B 17/2841; A61B 2017/2837
USPC ...................................... 606/96–98, 205–209
See application file for complete search history.

(56) References Cited

U.S. PATENT DOCUMENTS

| 221,611 | A | * | 11/1879 | Ringstad | D07B 7/162 |
| | | | | | 269/256 |
| 2,181,746 | A | * | 11/1939 | Siebrandt | A61B 17/17 |
| | | | | | 408/115 R |
| 3,019,790 | A | * | 2/1962 | Militana | A61B 17/122 |
| | | | | | 604/116 |
| 4,312,337 | A | * | 1/1982 | Donohue | A61B 17/1796 |
| | | | | | 606/103 |
| 4,787,377 | A | * | 11/1988 | Laboureau | A61B 17/1714 |
| | | | | | 606/84 |
| 5,697,933 | A | * | 12/1997 | Gundlapalli | A61B 17/1714 |
| | | | | | 606/206 |
| 5,725,532 | A | * | 3/1998 | Shoemaker | A61B 17/1775 |
| | | | | | 623/1.11 |
| 5,817,098 | A | * | 10/1998 | Albrektsson | A61B 17/175 |
| | | | | | 606/96 |
| 8,236,001 | B2 | * | 8/2012 | Willi | A61B 17/175 |
| | | | | | 606/89 |

(Continued)

*Primary Examiner* — Eric S Gibson
(74) *Attorney, Agent, or Firm* — Norton Rose Fulbright US LLP

(57) ABSTRACT

Systems, methods, and devices provide for a bone centering drill guide. The bone centering drill guide may include a clamping mechanism which clamps to a bone in a pivotable fashion. The proximal end of the clamping mechanism includes a handle portion having a first arm and a second arm which is configured to allow a user to grip the device and exert force which urges the first and second arms toward each other. The distal end includes a clamping portion having first and second arms which are urged into a closed configuration when closing force is provided to the handle portion. The proximal end may further include a locking mechanism which locks the clamping device in a clamped configuration. The bone centering drill guide may further include a guide slot disposed on the distal end above the clamping arms, the slot configured to remain centered between the first and second clamping arms.

22 Claims, 8 Drawing Sheets

(56) References Cited

U.S. PATENT DOCUMENTS

| | | | | |
|---|---|---|---|---|
| 8,529,575 B2* | 9/2013 | Tsai | ................ | A61B 17/2804 606/89 |
| 8,900,241 B2* | 12/2014 | Willi | ................ | A61B 17/175 606/86 R |
| 2003/0212435 A1* | 11/2003 | Gold | ................ | A61B 17/122 606/206 |
| 2004/0176779 A1* | 9/2004 | Casutt | ................ | A61B 17/1757 606/102 |
| 2004/0220582 A1* | 11/2004 | Keller | ................ | A61F 2/4611 606/99 |
| 2005/0038444 A1* | 2/2005 | Binder, Jr. | ................ | A61B 17/1728 606/96 |
| 2008/0183179 A1* | 7/2008 | Siebel | ................ | A61B 17/175 606/89 |
| 2008/0215057 A1* | 9/2008 | Willi | ................ | A61B 17/175 606/88 |
| 2009/0254130 A1* | 10/2009 | Wotton, III | ................ | A61B 17/17 606/324 |
| 2010/0125277 A1* | 5/2010 | Dace | ................ | A61B 17/1757 606/96 |
| 2012/0123428 A1* | 5/2012 | Berberich | ................ | A61B 17/17 606/96 |
| 2012/0197291 A1* | 8/2012 | Tsai | ................ | A61B 17/2804 606/205 |
| 2013/0079789 A1* | 3/2013 | Randle | ................ | A61B 17/1767 606/96 |
| 2015/0005779 A1* | 1/2015 | Tepic | ................ | A61B 17/28 606/96 |
| 2015/0100080 A1* | 4/2015 | Kohler | ................ | A61B 17/8866 606/205 |
| 2015/0374425 A1* | 12/2015 | Hashmi | ................ | A61B 17/8866 606/105 |
| 2018/0049757 A1* | 2/2018 | Bettenga | ................ | A61F 2/4644 |
| 2019/0046235 A1* | 2/2019 | Waisman | ................ | A61B 17/3472 |

* cited by examiner

BONE CENTERING DRILL GUIDE

CROSS-REFERENCE TO RELATED APPLICATION

The present application claims priority to U.S. Provisional Application No. 62/387,220 filed Dec. 23, 2015 and entitled "BONE CENTERING DRILL GUIDE," the disclosure of which is incorporated by reference herein in its entirety.

TECHNICAL FIELD

The present application relates to drill guides for use in surgical procedures. More particularly, the present application is directed to drill guides mounted to a bone clamping device which provides for precise positioning of the drill guide.

BACKGROUND

During surgical procedures the need often arises to drill a hole into a bone. Such holes may be used in various contexts. For example, a hole may be drilled into a bone in order to facilitate the insertion of a K-wire or to act as a pilot hole for later inserted objects such as screws or other fixation devices. When drilling a hole into a bone it is often preferred to locate and drill into the center of the bone. Utilizing the center of a bone maximizes the structural strength and capabilities of the bone. It also helps to prevent cracking or chipping of a bone structure during the surgical procedure, which can lead to undesired complications.

It may also be preferred to have a bone clamping device which is able to clamp onto a bone that is the subject of a particular surgical procedure. This clamping device may carry a drill guide apparatus in a manner that allows a surgeon to utilize the drill guide while the overall surgical instrument is held in place. Prior art clamping devices which are able to carry a drill guide have previously included overly complex mechanisms to maintain the drill guide in its centered position while arms of a clamp move into a clamped to position. Other prior art devices have included centering mechanisms which protrude forward with respect to the handles of a clamping device. These centering mechanisms are prone to get in the way of a surgeon while operating or could make undesired contact with a patient when the drill guide and clamping device are attached at steep angles with respect to a bone. Still further, prior art devices have provided for clamping mechanisms with detachable/adjustable drill guide placement. These devices are also not preferred in some instances as they may overly complicate the surgical procedure being performed. It is further appreciated that more complicated designs are also often more difficult to sterilize post-operation.

BRIEF SUMMARY

The present invention is directed to systems, methods, and devices which provide for a bone centering drill guide. In one embodiment the bone centering drill guide may include a clamping mechanism which clamps to a bone in a scissor-like pivotable fashion. The clamping mechanism includes a first and second arm having a proximal end and a distal end. The proximal end includes a handle portion on the first and second arms which are configured to allow a user to grip the device and exert force which urges the first and second arms toward each other. The distal end includes a clamping portion on the first and second arms which are urged into a closed configuration when closing force is provided to the arms of the handle portion. A central pivot point may be provided on or near the distal end which connects the first and second arms and facilitates the scissor-like clamping arrangement. The proximal end may further include a locking mechanism which locks the clamping device in a closed (or clamped) configuration.

In one embodiment, the bone centering drill guide may further include a guide portion having a guide slot disposed on the distal end above the clamping arms, the slot configured to remain centered between the first and second clamping arms. The centered arrangement may be facilitated by a fixation means which affixes the guide portion to the clamping mechanism.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1:
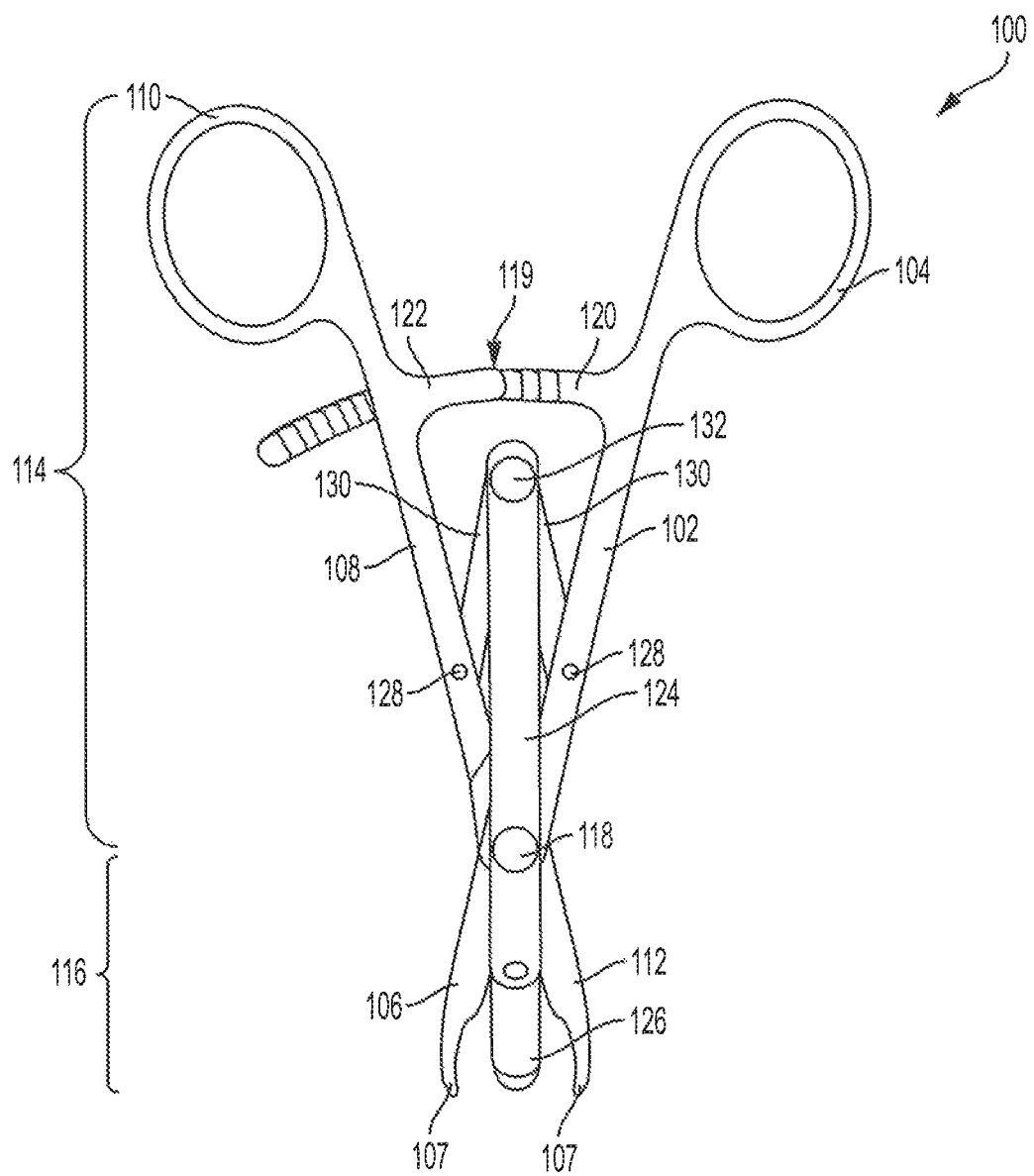
FIG. 1 is a top view of a bone centering drill guide in accordance with an embodiment of the present application.
Figure 2:
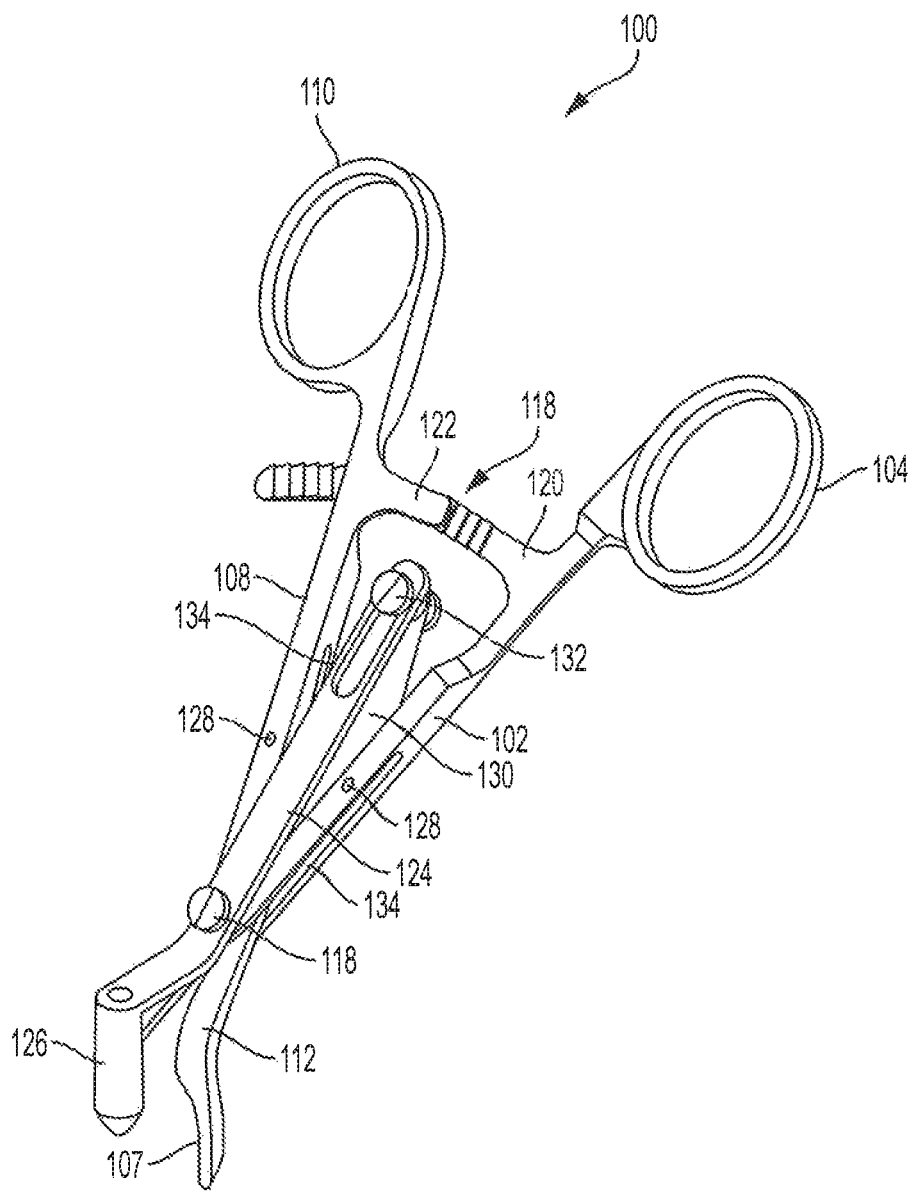
FIG. 2 is a perspective view of a bone centering drill guide in accordance with an embodiment of the present application.
Figure 3:
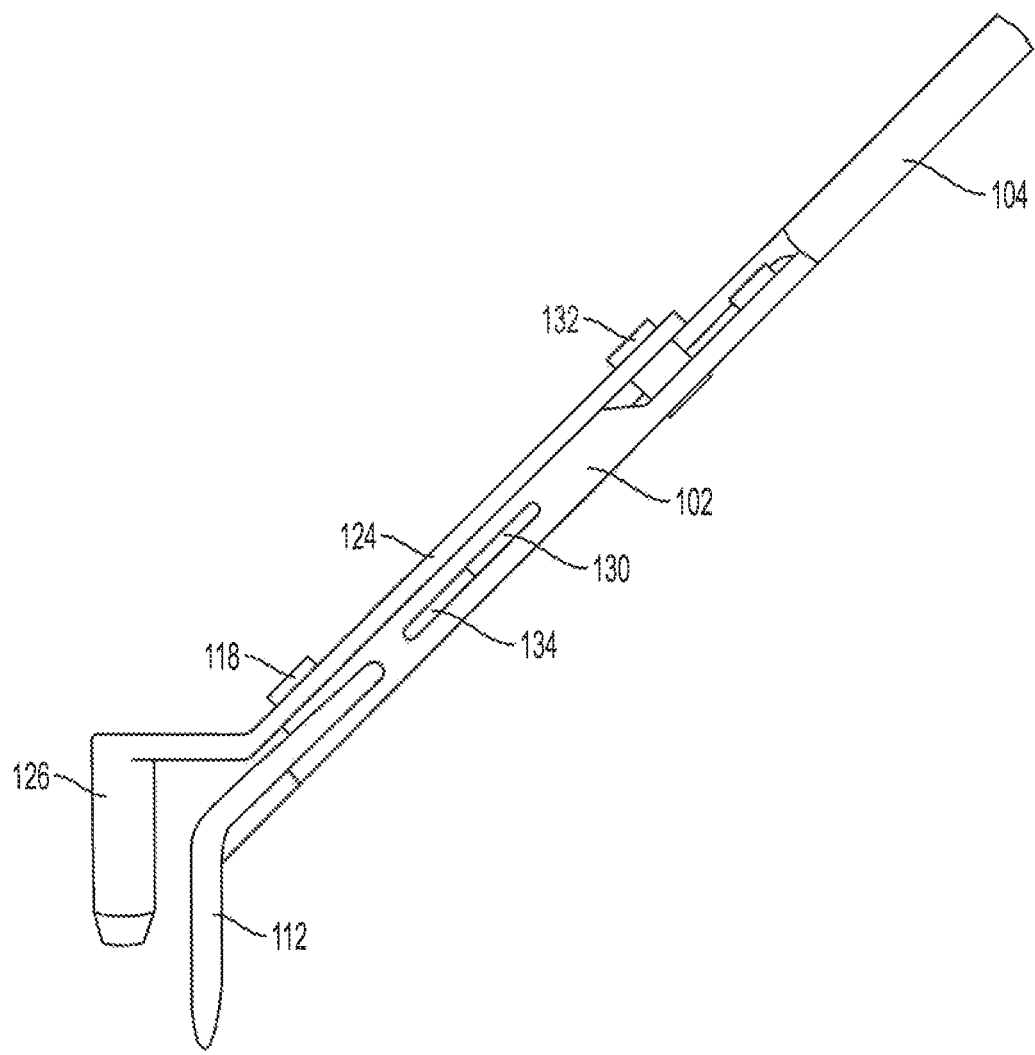
FIG. 3 is a side view of a bone centering drill guide in accordance with an embodiment of the present application.
Figure 4:
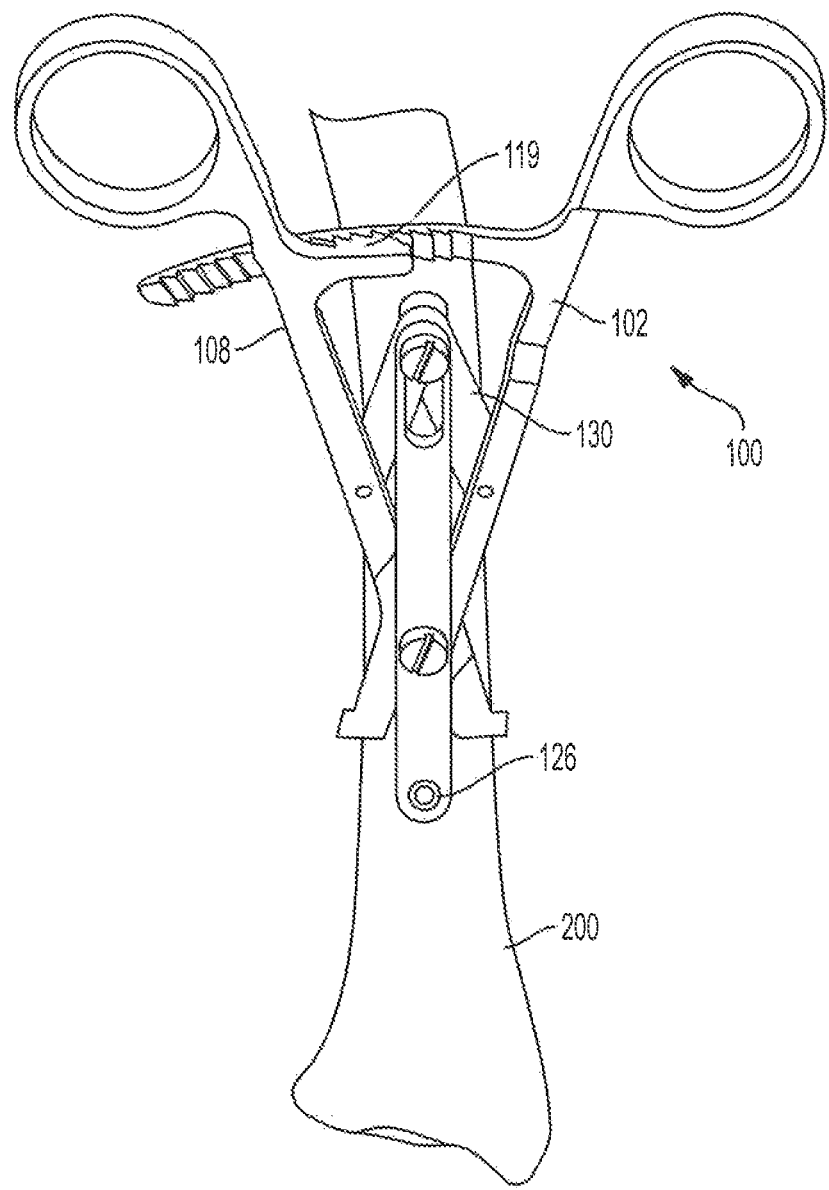
FIG. 4 is a view of a bone centering drill guide while clamped to a bone in accordance with an embodiment of the present application.
Figure 5:
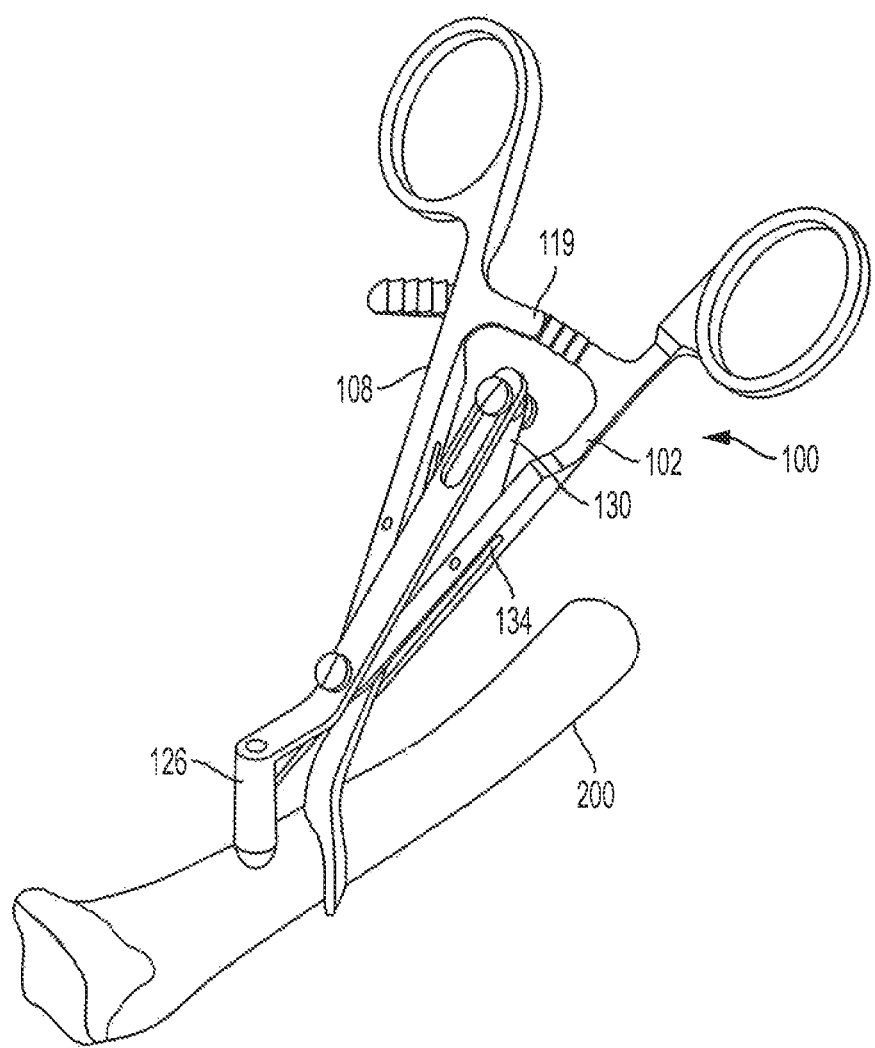
FIG. 5 is a view of a bone centering drill guide while clamped to a bone in accordance with an embodiment of the present application.
Figure 6:
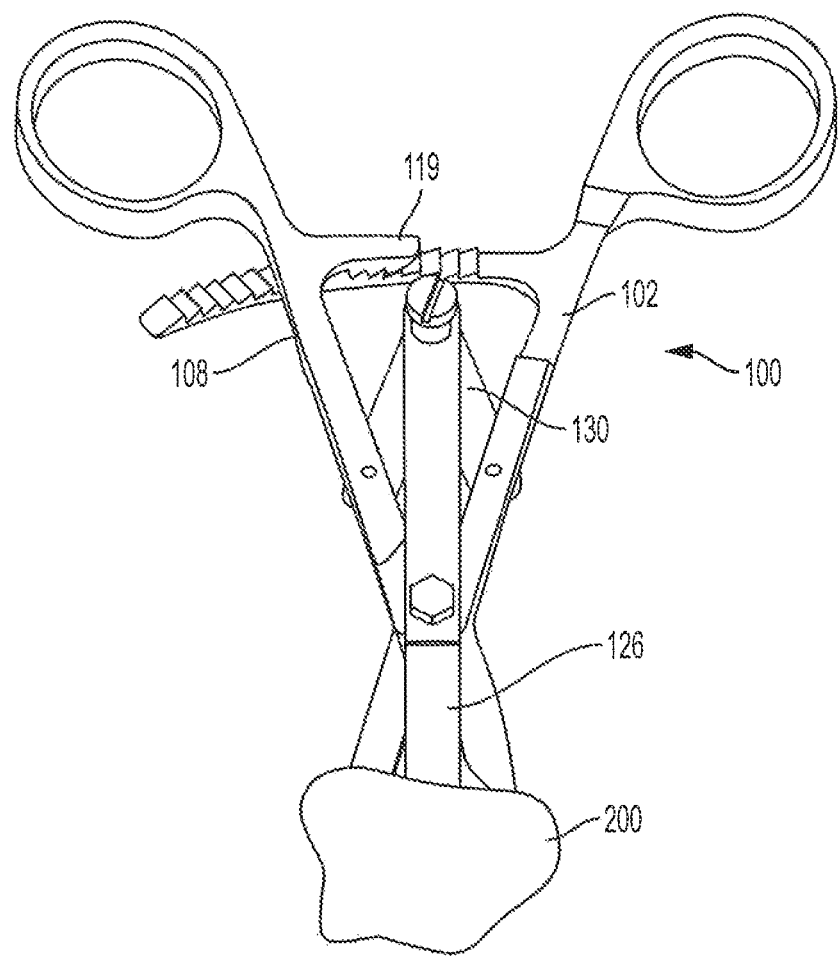
FIG. 6 is a view of a bone centering drill guide while clamped to a bone in accordance with an embodiment of the present application.
Figure 7:
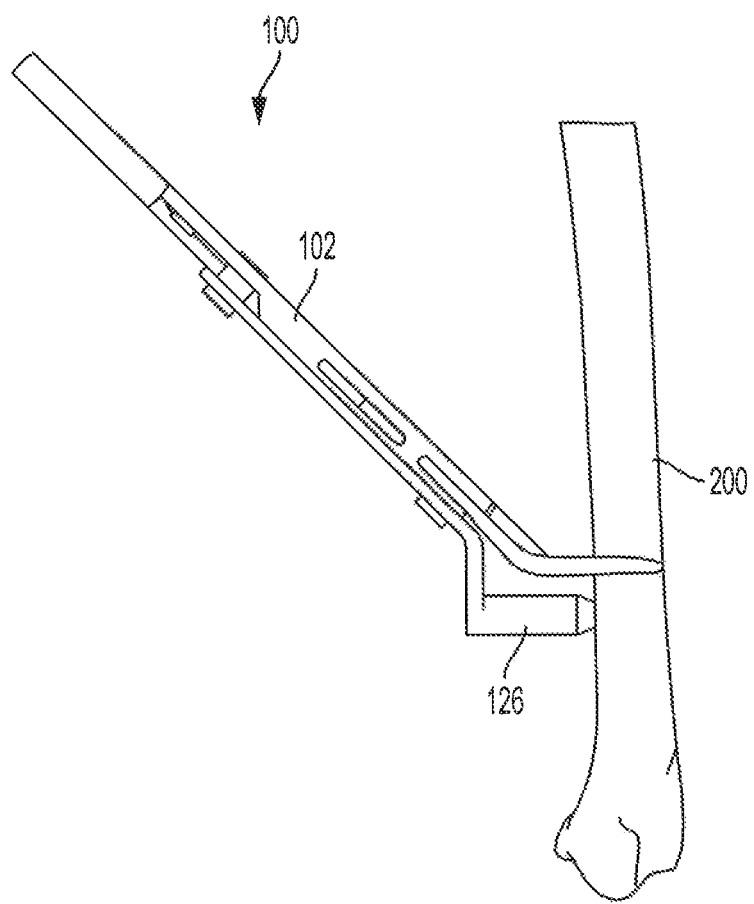
FIG. 7 is a view of a bone centering drill guide while clamped to a bone in accordance with an embodiment of the present application and FIG. 8 is a method of making and using the above-described bone centering drill guides.

FIGS. 1-3 illustrate a bone centering drill guide 100 in accordance with an embodiment of the present application.

Drill guide 100 includes a first arm 102 having a handle portion 104 and a clamping portion 106. Drill guide 100 further includes a second arm 108 having a second handle portion 110 and a second clamping portion 112. Handle portions 104 and 110 may include one or more finger holes to facilitate gripping of drill guide 100, or may include any other equivalent feature that accomplishes such functionality. Clamping portion 106 and 112 may include inner surfaces 107 (shown as being radially curved in the illustrated embodiment) which are configured to make contact with a bone surface. In some embodiments, inner surfaces 107 may include gripping members, such as teeth, which provide for a more secure grip when in a clamped position. In some embodiments, the shape of the inner surfaces 107 may be configured to match the curvature and/or size of a particular bone on which drill guide 100 will be used. It is appreciated that while inner surfaces 107 are illustrated as being symmetrical, in some embodiments the inner surface 107 of clamping portion 106 may be shaped different than that of clamping portion 112. These shape differences may include different radii of curvature, may cause one or more of the inner surfaces to have no curvature, and in some embodiments may require that one inner surface be longer than the other inner surface. Such adjustments may be made in order to create a more universally fit tool, or may be made to facilitate bone-specific design functionality.

Drill guide 100 may also be characterized as having a proximal end 114 and distal end 116 wherein the handle portions 104 and 110 are located in the proximal end 114 and the clamping portions 106 and 112 are located at the distal end 116.

First arm 102 and second arm 108 are pivotably attached at connection/pivot point 118. The attachment at connection point 118 attaches first arm 102 and second arm 108 in a manner that causes the longitudinal axes of the arms to intersect. Accordingly, first arm 102 and second arm 108 are disposed in a scissor-like arrangement.

In one embodiment, drill guide 100 further includes a locking mechanism 119 located on proximal end 114 of drill guide 100. Locking mechanism 119 may be configured to provide a locking or clamping force after sufficient pressure forces have urged handle portion 110 and handle portion 104 toward each other. Such a locking force may be utilized to allow a user of drill guide 100 to clamp the tool in place on a bone while still being able to utilize his or her hands for other aspects of a surgical procedure. As illustrated, locking mechanism 119 includes a first protrusion 120 extending from arm 102 and a second protrusion 122 extending from arm 108. The first protrusion 120 has upwardly oriented teeth, while second protrusion 122 has downwardly oriented teeth. When a locking force is applied the upwardly oriented teeth create an interference or zip fit which locks drill guide 100 in a closed or partially closed position (depending on the extent that the clamping three has urged handles 104 and 110 toward each other). In one embodiment, locking mechanism 119 may be configured such that it is sufficiently flexible to allow a user to lift at least one protrusion in order to allow for the locked configuration (e.g. zip fit) to release so that the handles may be opened outward.

It is appreciated that the illustrated locking mechanism 119 provides for a substantially continuous locking length. In other words, drill guide 100 with this particular locking mechanism may be utilized on different widths of bone because use on a larger bone would reduce the distance that handles 104 and 110 may be urged toward each other, but the overlap of first protrusion 120 will still allow contact with second protrusion 122 and therefore the locking mechanism 119 will still be engaged in a locked position. In other embodiments, locking mechanism 119 may be configured to provide a lock only at one or more particular clamping widths. It is further appreciated that embodiments may utilize any type of locking mechanism or attachment that is sufficient to allow for the maintenance of a clamping force when handles 104 and 110 have been urged into a clamping position.

Bone centering drill guide 100 further includes a drill guide assembly 124. Drill guide assembly 124 includes a proximal end and a distal end. The distal end includes drill guide tube 126 which is configured to facilitate the insertion of a drill bit or any other drilling tool, pin, or guide wire that may be used with bone centering drill guide 100 in the course of a surgical proceeding. It is appreciated that drill guide tube 126 may be implemented using different diameters according to the needs of an end user. And in some embodiments drill guide tube 126 may include inserts that reduce the diameter or may be interchangeable with different sized tubes. It is further appreciated that, as illustrated, arms 102 and 108 are disposed along a planar axis, and guide tube 126 is elevated with respect to the planar axis. Additionally, guide tube 126 defines a longitudinal axis extending through the tube which intersects with the planar axis of arms 102 and 108. In this configuration, drill guide 100 may be held in a manner that allows the tool to be out of the working area of a user attempting to work with or through guide tube 126.

Drill guide assembly 124 is attached and maintained on bone centering drill guide 100 in order to provide for a fixed position with respect to the inner surfaces 107 of clamping portions 106 and 112. In the illustrated embodiment, drill guide tube 126 remains centered between inner surfaces 107. However it is appreciated that some embodiments may offset drill guide tube 126 such that it is not in a centered position, while maintaining it in a fixed. position with respect to inner surfaces 107. This may be done in circumstances where it is more desirable to drill closer to one side of a bone than another.

Drill guide assembly 124 may be attached to first and second arms 102 and 108 at connection point 118 and arm connection in points 128. Arm connection points 128 connect first and second arms 102 and 108 to v-shaped arms 130 of drill guide assembly 124. The base of the v-shaped arms 130 are located on the proximal end of drill guide assembly 124 and includes a slidably coupled connection point 132 which is configured to traverse a slot in drill guide assembly 124 wherein first arm 102 and second arm 108 are actuated with respect to each other.

In the illustrated embodiment connection points 128, v-shaped arms 130, and connection point 132 are disposed on the proximal side of connection/pivot point 118. Such a design allows for these aspects of drill guide assembly 124 to be out of the way of the working surface that may need to be accessed by a surgeon. Further, it allows for drill guide tube 126 to be held at steeper angles with respect to the working surface (which can include bone, skin, muscle tissue, etc.) without having portions of drill guide assembly 124 interfere with the working surfaces. Connection points 128 may be disposed on the top or bottom surface of first and second arms 102 108 in a manner that allows at least a portion of v-shaped arms to at least partially overlap the inner side wall of first and second arms 102 108, where the overlap increases/decreases at the connection point when the v-shaped arms are pivoted along the connection point upon the guide tool 100 being closed/opened during use.

In one aspect arms 102 and 108 may further include slot-like apertures 134 along the inner surfaces of the arms 102 and 108. These slot-like apertures allow for v-shaped arms 130 to at least partially nest within arms 102 and 108. In this configuration, bone centering drill guide 100 is able to come to more of a narrowly clamped position because as arms 102 and 108 are urged toward each other, the width of v-shaped arms 130 narrows. Without slot like apertures 134, the v-shaped arms 130 would come into contact with the inner surface of arms 102 and 108 at an earlier point in time and therefore arms 102 and 108 would be restricted from further travel toward each other. Such a design also allows for drill guide assembly to be smaller in size with respect to the overall device 100 which allows for more compact handles and shorter length (e.g. because v-shaped 130 arms may need to be longer absent apertures 134). Further, drill guide assembly 124 is able to be disposed on guide 100 such that it is substantially clear of the working area of the user.

FIGS. 4-7 illustrate bone centering clamping tool 100 for use in clamping bone 200 in a manner which disposes drill guide tube 126 in the center of bone 200. As illustrated, inner surfaces 107 are in contact with bone 200. Additionally, locking mechanism 119 is in a locked or engaged configuration. Arms 102 and 108 have been urged toward each other sufficiently close that portions of v-shaped arms 130 are nested within slots 134. Further, the work space near the bone surface is not encumbered by aspects of drill guide assembly 124.

Figure 8:
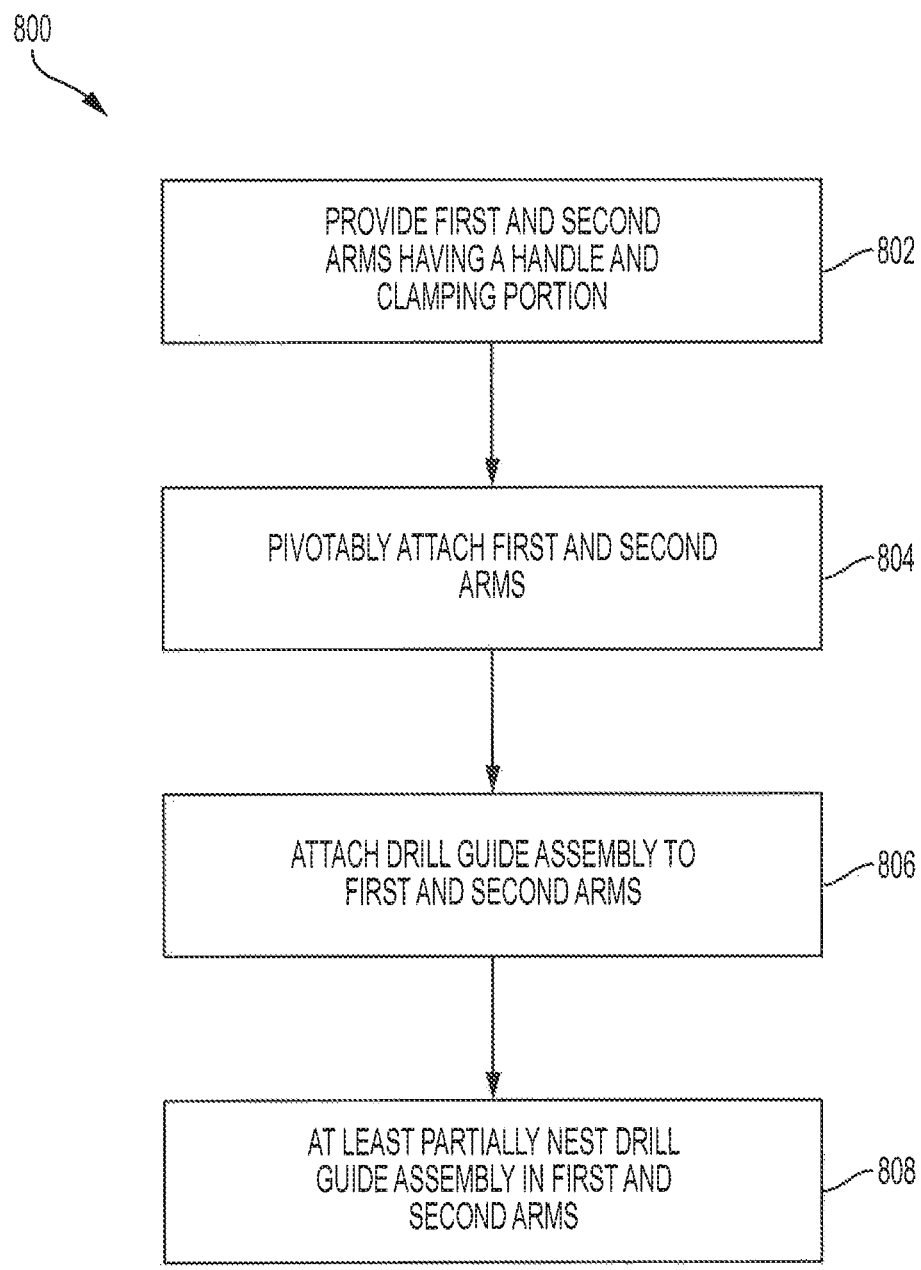

Embodiments of the present application may also be directed towards methods of making and using the above-described bone centering drill guides. For example, as shown in FIG. 8, method 800 of making such a guide may include providing a first and second arm having respective handle and clamping portions 802; pivotably attaching said first and second arms to dispose the arms in a scissor-like arrangement 804; attaching a drill guide assembly having a proximal end and a distal end 806, where the proximal end is attached to the drill guide arms and includes v-shaped arms configured to open and close with the drill guide arms and at least partially nesting within the drill guide arms as the drill guide arms approach a closed position 808. Methods of using will include the use of a bone centering guide as described above, the implementation of such methods will be apparent to a person of ordinary skill in the art in view of the above description. For example, a user may grasp handle portions 103 and 110 and cause inner surfaces 107 to be urged to an open position. A bone may be moved between inner surfaces 107 at a location that causes the tip of guide 126 to be placed proximate to a drilling location of the bone. Handles 104 and 110 may then be urged to place inner surfaces in a clamped configuration on the bone for use while locking mechanism 119 holds drill guide 100 in its closed/clamped position for use.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

What is claimed is:

1. An apparatus comprising:
a first and second arm having a proximal end and a distal end, the proximal end of the first and second arms including a handle portion, and a locking mechanism configured to allow the first and second arms to be held together in a locked configuration, the distal end of the first and second arms including a clamping portion configured to clamp a bone surface between the first and second arms;
a connection portion configured to connect the first and second arm in an intersecting manner and pivotably couple the first and second arms in a scissor-like arrangement;
a guide assembly having a proximal and distal end, the distal end including a guide tube configured to facilitate a device to be guided along an orientation of the guide tube, the proximal end of the guide assembly including a plurality of connection points which connect the guide assembly to the first and second arms respectively, the proximal end further comprising v-shaped arms connected at the connection points, wherein at least a portion of the v-shaped arms are configured to overlap with a side wall of at least one of the first and second arms when the arms approach a clamped configuration.

2. The apparatus of claim 1 wherein a locking portion comprises a first extension extending from the proximal end of the first arm and a second extension extending from the proximal end of the second arm; wherein said extensions include a coupling structure configured to couple the extensions together to lock the apparatus.

3. The apparatus of claim 2 wherein the first extension and second extension comprise opposing-faced ridges configured to mate to facilitate locking of the first and second arms.

4. The apparatus of claim 2 wherein at least one of the first extension and second extension are configured to be sufficiently flexible to be pulled apart to release the apparatus from a locked configuration.

5. The apparatus of claim 1 wherein the clamping portion comprises one or more inner surfaces having teeth configured to grip the one surface.

6. The apparatus of claim 1 wherein the guide assembly is configured to dispose the guide tube in a fixed location with respect to the distal end of the first and second arms.

7. The apparatus of claim 6 wherein the fixed location is centered between the first and second arms.

8. The apparatus of claim 1 wherein the first and second arms are disposed on a planar axis and the guide tube is elevated with respect to the planar axis.

9. The apparatus of claim 8 wherein the guide tube defines a longitudinal axis that intersects the planar axis.

10. The apparatus of claim 1 wherein the proximal end of the guide assembly attaches to the apparatus at the connection portion.

11. The apparatus of claim 1 wherein the v-shaped arms are configured to at least partially nest within an aperture of the side wall of at least one of the first and second arms when the arms approach a clamped configuration.

12. A method of making a guide tool, said method comprising:
providing a first arm and a second arm, said first and second arms including respective proximate ends having handle portions and distal ends having clamping portions;
pivotably attaching said first and second arms at an attachment point to dispose the arms in a scissor-like arrangement;
attaching a drill guide assembly having a proximal end and a distal end, where the proximal end of the drill guide assembly is attached to the first and second arms and at the attachment point; and
attaching a first v-shaped arm of the drill guide assemble to the first arm and a second v-shaped arm to the second arm in a manner wherein said first and second v-shaped arms are configured to at least partially overlap a side wall of the first and second arms when closing said clamping portions of the guide tool.

13. The method of claim 12 wherein the first and second arms include at least one locking portion configured to lock the first and second arms in a clamped position.

14. The method of claim 13 wherein the locking portion comprises a first extension extending from a proximal end of the first arm and a second extension extending from a proximal end of the second arm; wherein said extensions include a coupling structure configured to couple the extensions together to lock the apparatus.

15. The method of claim 14 wherein the first extension and second extension comprise opposing-faced ridges configured to mate to facilitate locking of the first and second arms.

16. The method of claim 13 wherein at least one of the first extension and second extension are configured to be sufficiently flexible to be pulled apart to release the apparatus from a locked configuration.

17. The method of claim 12 wherein the clamping portion comprises one or more inner surfaces having teeth configured to grip the bone surface.

18. The method of claim 12 wherein the guide assembly is configured to dispose the guide tube in a fixed location with respect to the distal end of the first and second arms.

19. The method of claim 18 wherein the fixed location is centered between the first and second arms.

20. The method of claim 12 wherein the first and second arms are disposed on a planar axis and the guide tube is elevated with respect to the planar axis.

21. The method of claim 20 wherein the guide tube defines a longitudinal axis that intersects the planar axis.

22. The method of claim 12 wherein the v-shaped arms are configured to at least partially nest within the side wall of the first and second arms when closing said clamping portions of the guide tool.

* * * * *

UNITED STATES PATENT AND TRADEMARK OFFICE
CERTIFICATE OF CORRECTION

PATENT NO. : 10,543,004 B2  
APPLICATION NO. : 15/389399  
DATED : January 28, 2020  
INVENTOR(S) : Randall W. Viola et al.

Page 1 of 1

It is certified that error appears in the above-identified patent and that said Letters Patent is hereby corrected as shown below:

In the Specification

Column 3, Line 54, delete "clamping three" and replace with --clamping force--.

In the Claims

Column 6, Claim 5, Line 50, delete "grip the one surface" and replace with --grip the bone surface--.

Signed and Sealed this  
Thirtieth Day of June, 2020

Andrei Iancu  
*Director of the United States Patent and Trademark Office*